United States Patent

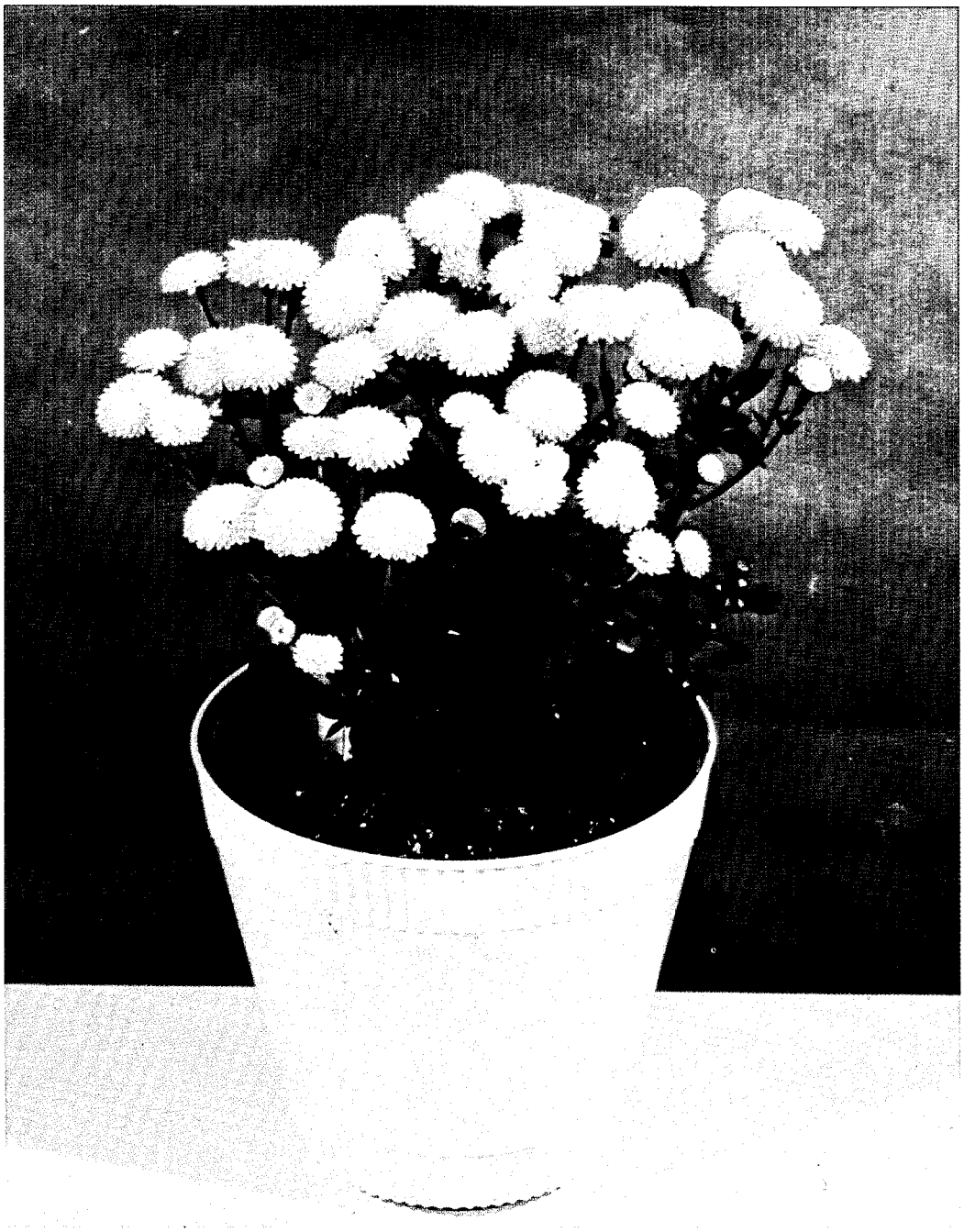

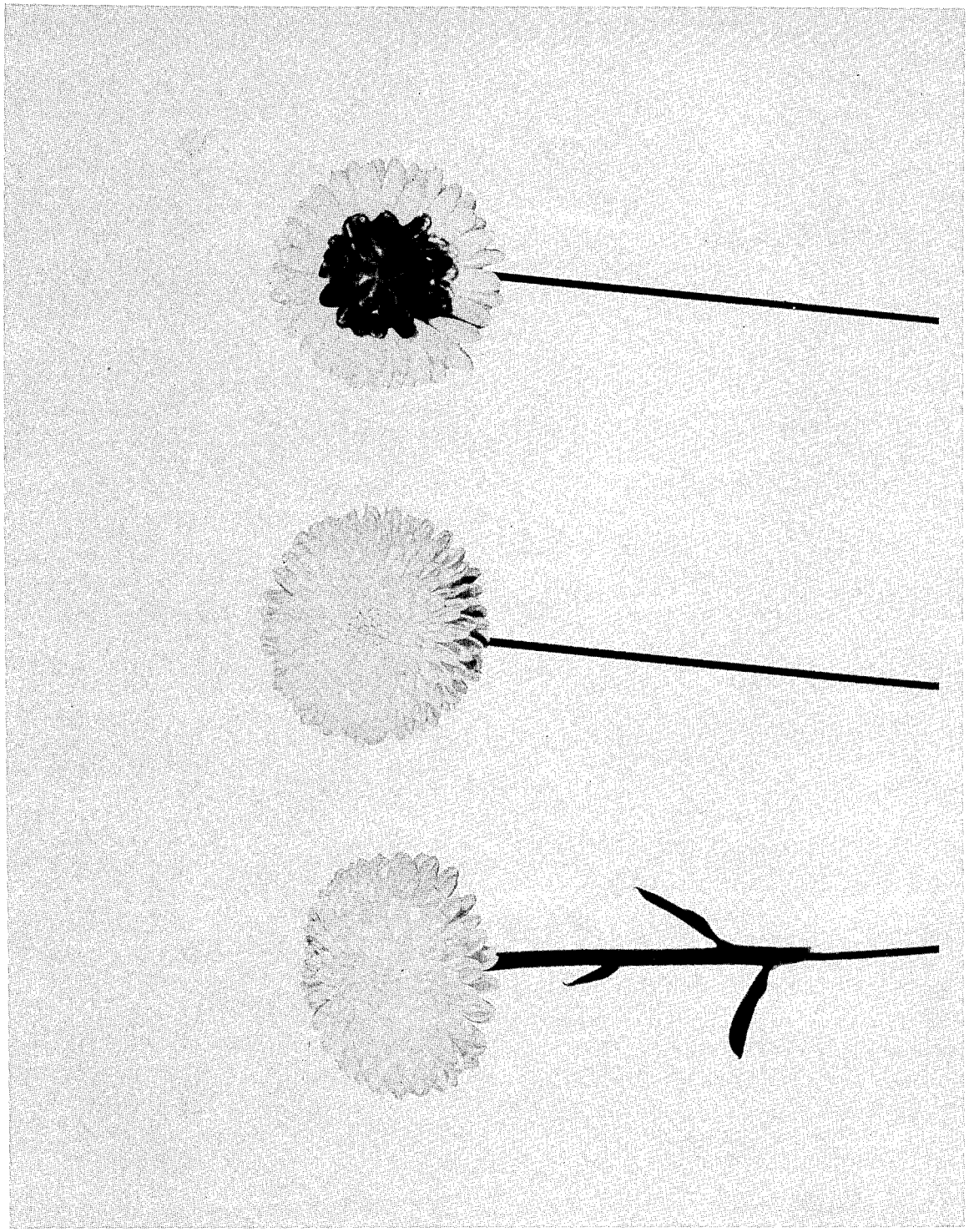

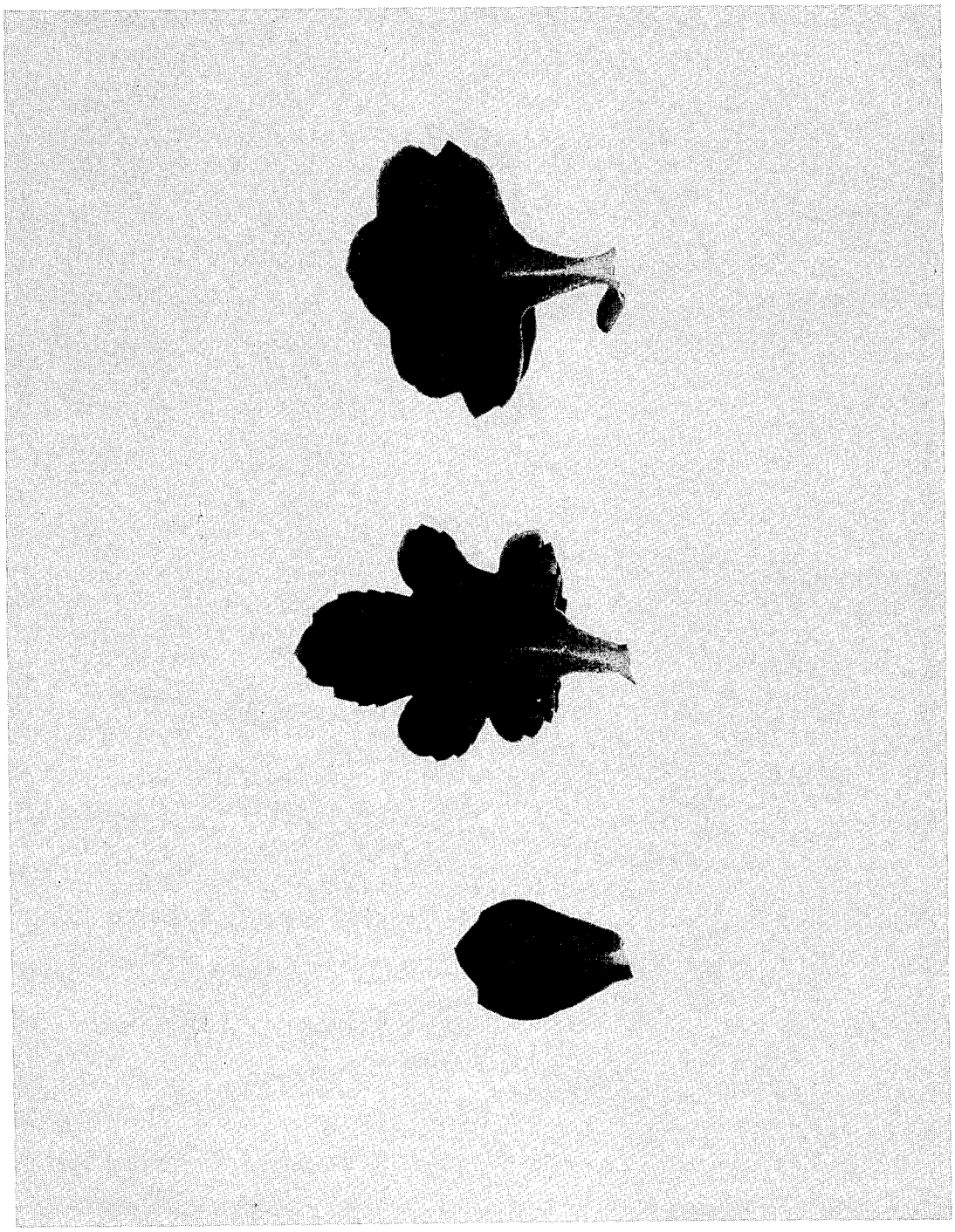

Plant Pat. 3,970
Patented Oct. 26, 1976

3,970

CHRYSANTHEMUM PLANT

Grace H. Mack, 108 Wahackme Road, New Canaan, Conn. 06840, and William E. Duffett, Akron, and Walter H. Jessel, Jr., Doylestown, Ohio; said Duffett and Jessel assignors to said Mack Filed Oct. 6, 1975, Ser. No. 619,919
Int. Cl.[2] A01H 5/00
U.S. Cl. Plt.—77 1 Claim The present invention comprises a new and distinct cultivar of *Chrysanthemum morifolium*, Ramat., hereinafter referred by the cultivar name Pearls (#73007M03).

Pearls is a product of a planned breeding program which had the objective of creating cultivars with small pompon inflorescence type, short height, spreading branching pattern, durable inflorescence, short (six to seven week) flowering response period, and adaptability to both natural season outdoor flowering and controlled greenhuse flowering programs.

Pearls was riginated from a cross made by Grace H. Mack in a controlled breeding program in New Canaan, Conn. in the year 1972. The male, or pollen parent, was 25–70 (#21730E05; unnamed seedling), an off-white pompon (button) originated by the present inventors from a cross between Snowbound (#21680E09; unpatented; commercially available) and 942 (#21710E21; unnamed seedling). The female, or seed parent of Pearls, was #70011M01 (unnamed seedling), a yellow pompon originated by the present inventors from a cross between Classic (#67256M01; U.S. Plant Pat. No. 3,460) and 655 (#21670E01; unnamed seedling). Classic, 942, and 655 were products of the breeding program of the present inventors.

Pearls was discovered and selected as a flowering plant within the progeny of the stated cross by Walter H. Jessel, Jr. on May 2, 1973 in an outdoor filed in Fort Myers, Florida.

The first act of asexual reproduction of Pearls was accomplished when vegetative cuttings were taken from the initial selection in July, 1973 in a controlled environment in Barberton, Ohio by a technician working under formulations established and supervised by William E. Duffett and Walter H. Jessel, Jr. Horticultural examination of selected units initiated October 23, 1973 has demonstrated that the combination of characteristics as herein disclosed for Pearls are firmly fixed and are retained through successive generations of asexual reproduction. Pearls has not been observed under all possible environmental conditions. The phenotype may vary significantly with variations in environment such as temperature, light intensity, and daylength. The following observations, measurements, and comparisons describe plants grown in a field in Barberton, Ohio under conditions which are generally described in *Local Climatological Data, Annual Summary with Comparative Data, Akron, Ohio.* U.S. Department of Commerce, National Oceanic and Atmospheric Administration, Environmental Data Service, Washington, D.C., 1973, 1974, and *Tables of Sunrise, Sunset, and Twilight.* Supplement to the American Emphemeris, 1946, U.S. Naval Observatory, Washington, D.C., p. 103.

The following traits have been repeatedly observed and are determined to be basic characteristics of Pearls which in combination distinguish this chrysanthemum as a new and distinct cultivar:

(1) Flat inflorescence form.
(2) Pompon inflorescence type.
(3) White inflorescence color.
(4) Diameter across face of inflorescence up to one inch.

(5) Permanence of inflorescence ranging from 21 to 28 days.
(6) Short plant height.
(7) Semi-spreading branching pattern.
(8) Dark green foliage color.
(9) Average natural season flowering date of October 1.
(10) Average flowering response period of 7 weeks in photoperiodic controlled flowering programs.

The accompanying photographic drawings show typical inflorescence and foliage characteristics of Pearls with colors being as nearly true as possible with illustrations of this type. Sheet 1 is a color photograph of Pearls. Sheet 2 is a black and white photograph showing three views of the inflorescence of Pearls. Sheet 3 is a black and white photograph showing the foliage of Pearls at three stages of growth.

Of the many commercially available cultivars known to the present inventors, the most similar existing cultivar is Baby Tears (#21680E05; unpatented). Reference is made to attached Chart A which compares certain characteristics of Pearls with the same characteristics of Baby Tears, Pearls has different inflorescence color, later natural season flower date, different branching pattern, and darker foliage color. The inflorescence form, inflorescence type, and diameter across face of inflorescence of Pearls are similar to those of Baby Tears.

In the following description, color references are made to The Munsell Limit Color Cascade, 1972 edition. The color values were determined between 8:30 and 9:00 a.m. on June 27, 1975 under 150 foot-candle light intensity at Barberton, Ohio. Plants for this purpose were grown and flowered in a greenhouse at Barberton, Ohio.

Botanical classification: *Chrysanthemum morifolium*, Ramat., cv Pearls.

I. INFLORESCENCE

A. *Capitulum*

*Form:* flat.
*Type:* pompon.
*Permance:* 21–28 days.
Diameter across face: 0.8 to 1.0 inch.

B. *Corolla of ray floret*

*Texture (adaxial):* glabrous.
*Appearance and form:* ligulate.
*Arrangement:* whorled on receptacle.
*Persistence:* resists shatter.
*Color (abaxial):* 26–2 to white.
*Color (adaxial):* white.

C. *Reproductive organs*

*Androecium:* present disc florets; syngenesious stamen; scant pollen.
*Gynoecium:* present both ray and disc florets; inferior, bicarpellate ovary; single style; two-lobed stigma.

II. PLANT

A. *General appearance*

Semi-spreading; short height.

B. *Duration and texture*

Herbaceous; perennial.

C. *Foliage*

*Color (abaxial):* between 20–15 and 20–16.
*Color (adaxial):* 20–13 overcast with white.
*Shape:* spatulate; deeply lobed.
*Texture:* glabrous.
*Arrangement:* alternate.
*Veination:* prominent.
*Margin:* moderately serrated.

CHART A—COMPARISON OF PEARLS AND BABY TEARS

| Cultivar | Inflorescence color | Inflorescence form and type | Natural season flower date | Branching pattern | Foliage color | Diameter across face of inflorescence |
|---|---|---|---|---|---|---|
| Pearls | White | Flat pompon | October 1 | Semispreading | Dark green | 1 inch. |
| Baby tears | Ivory white | do | September 20 | Spreading | Medium green | Do. |

NOTE.—Comparisons made of plants grown under natural season outdoor field conditions in Barberton, Ohio.

We claim:

1. A new and distinct cultivar of chrysanthemum known by the cultivar name Pearls and characterized particularly as to uniqueness by the combined characteristics of flat inflorescence form; pompon inflorescence type; white inflorescence color; diameter across face of inflorescence up to one inch; permanence of inflorescence ranging from 21 to 28 days; short plant height; semispreading branching pattern; dark green foliage color; average natural season flowering date of October 1, and average flowering response period of 7 weeks in photoperiodic controlled flowering programs.

No references cited.

ROBERT E. BAGWILL, Primary Examiner